United States Patent
Lee et al.

(10) Patent No.: US 9,717,480 B2
(45) Date of Patent: **\*Aug. 1, 2017**

(54) METHOD OF VERIFYING A SURGICAL OPERATION IMAGE MATCHING AND METHOD OF COMPENSATING A SURGICAL OPERATION IMAGE MATCHING

(71) Applicants: KOH YOUNG TECHNOLOGY INC., Seoul (KR); KYUNGPOOK NATIONAL UNIVERSITY INDUSTRY—ACADEMIC COOPERATION FOUNDATION, Daegu (KR)

(72) Inventors: Hyun-Ki Lee, Daegu (KR); Min-Young Kim, Daegu (KR); Jae-Heon Chung, Gwangmyeong-si (KR)

(73) Assignees: KOH YOUNG TECHNOLOGY INC., Seoul (KR); KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 247 days.

This patent is subject to a terminal disclaimer.

(21) Appl. No.: 14/344,812

(22) PCT Filed: Apr. 22, 2013

(86) PCT No.: PCT/KR2013/003379
§ 371 (c)(1),
(2) Date: Mar. 13, 2014

(87) PCT Pub. No.: WO2013/165111
PCT Pub. Date: Nov. 7, 2013

(65) Prior Publication Data
US 2015/0051725 A1  Feb. 19, 2015

(30) Foreign Application Priority Data

Apr. 30, 2012 (KR) .................. 10-2012-0045349

(51) Int. Cl.
*G06F 19/00* (2011.01)
*A61B 8/08* (2006.01)
(Continued)

(52) U.S. Cl.
CPC ............ *A61B 8/5238* (2013.01); *G06F 17/50* (2013.01); *G06F 19/3437* (2013.01);
(Continued)

(58) Field of Classification Search
CPC ........... A61B 8/00; A61B 90/36; A61B 90/37; A61B 8/5238; A61B 2090/366
See application file for complete search history.

(56) References Cited

U.S. PATENT DOCUMENTS 5,823,958 A * 10/1998 Truppe .................. A61B 90/36
128/898
2003/0038921 A1 * 2/2003 Neal .................... A61B 3/1015
351/212

(Continued)

FOREIGN PATENT DOCUMENTS

JP     2004-275334    10/2004
KR     10-0942160    2/2010

OTHER PUBLICATIONS

Written Opinion of the International Searching Authority for International Application No. PCT/KR2013/003379, dated Aug. 24, 2013.

(Continued)

*Primary Examiner* — Tuan Vu
(74) *Attorney, Agent, or Firm* — Kile Park Reed & Houtteman PLLC

(57) ABSTRACT

In order to verify a surgical operation image matching, a model of a target is manufactured. Then, a reference body is attached to the model. Then, three-dimensional reference data regarding to the model is obtained. Then, grid patterned light is emitted onto the model to obtain reflection image. Then, three-dimensional shape is measured from the reflection image, and measurement image is obtained from the three-dimensional shape. Then, the measurement image and previously obtained three-dimensional reference data are matched. Then, reference position of the target in the three-dimensional reference data is compared with estimated position of the target, which is estimated by the reference body in the measurement image. Therefore, the matching of the surgical operation can be verified.

7 Claims, 6 Drawing Sheets

(51) Int. Cl.
G09B 23/28 (2006.01)
G06F 17/50 (2006.01)
A61B 90/00 (2016.01)
A61B 34/10 (2016.01)

(52) U.S. Cl.
CPC ........ *G09B 23/28* (2013.01); *A61B 2034/105* (2016.02); *A61B 2090/364* (2016.02)

(56) References Cited

U.S. PATENT DOCUMENTS

| | | | |
|---|---|---|---|
| 2003/0199765 A1* | 10/2003 | Stetten | A61B 8/00 600/439 |
| 2005/0008126 A1 | 1/2005 | Juh et al. | |
| 2005/0148854 A1* | 7/2005 | Ito | A61B 1/00149 600/407 |
| 2008/0103390 A1* | 5/2008 | Contag | G01N 21/6428 600/427 |
| 2008/0123927 A1* | 5/2008 | Miga | G06T 7/0032 382/131 |
| 2009/0125242 A1* | 5/2009 | Choi | G01N 21/45 702/19 |
| 2010/0256504 A1* | 10/2010 | Moreau-Gaudry | A61B 5/0066 600/476 |
| 2011/0230710 A1 | 9/2011 | Hoeg et al. | |

OTHER PUBLICATIONS

International Search Report for International Application No. PCT/KR2013/003379 dated Aug. 24, 2013.

* cited by examiner

PREVIOUS MATCHING

METHOD OF VERIFYING A SURGICAL OPERATION IMAGE MATCHING AND METHOD OF COMPENSATING A SURGICAL OPERATION IMAGE MATCHING

TECHNICAL FIELD

The present invention relates to a method of verifying a surgical operation image matching and a method of compensating a surgical operation image matching, and more particularly to a method of verifying a surgical operation image matching and a method of compensating a surgical operation image matching, which are capable of verifying or compensating a surgical operation image matching with accuracy through reduced time and cost.

BACKGROUND ART

Recently, a surgical operation of an affected area of a patient using a previously captured image is widely used. Especially, in a surgical operation of E.N.T. field, a high accuracy operation using a previously captured image is required since important nerves and organs should be avoided.

In general, the previously captured image include a three dimensional image such as an MRI image, a CT image, etc., and in order to perform matching the previously captured image with real-time captured image exactly, various methods for example a method of attaching a marker on a skin, a method using template, a method of surface template-assisted marker position (STAMP) have been studied.

However, according to the above conventional methods, there are various problems such as error induced by skin change when a marker is attached to the skin, an inconvenience and cost of making the stamp, a long time for matching, etc.

Therefore, a method of matching with high accuracy through reduced time and cost is required, and a method of verifying matching and a method of compensating matching are required.

DETAILED DESCRIPTION OF THE INVENTION

Objects of the Invention

Therefore, the objects of the invention is to provide a method of verifying a surgical operation image matching, which is capable of verifying a surgical operation image matching with accuracy through reduced time and cost.

The other object of the invention is to provide a method of compensating a surgical operation image matching, which is capable of compensating matching error of the surgical operation image.

Technical Solution

According to a method of verifying a surgical operation image matching, a model of a target is manufactured. Then, a reference body is attached to the model. Then, three-dimensional reference data regarding to the model with the reference body attached thereto is obtained. Then, grid patterned light is emitted onto the model with the reference body attached thereto to obtain reflection image regarding to the model with the reference body thereto. Then, three-dimensional shape is measured by applying bucket algorithm to the reflection image regarding to the model with the reference body attached thereto, and measurement image is obtained from the three-dimensional shape. Then, the measurement image and previously obtained three-dimensional reference data are matched with reference to a surface of the model. Then, reference position of the target in the three-dimensional reference data is compared with estimated position of the target, which is estimated by the reference body in the measurement image.

For example, the reference body may have a pole-shape, and a number of the reference body may be at least three.

For example, the three-dimensional reference data may be obtained from the model and at least one of CAD information regarding to the reference body and precise measurement information.

For example, after comparing reference position of the target in the three-dimensional reference data with estimated position of the target, which is estimated by the reference body in the measurement image, a position difference between the reference position of the target and the estimated position of the target may be calculated, and it may be checked if the position difference is within a reference value.

According to a method of compensating a surgical operation image matching, a model of a target is manufactured. Then, a reference body is attached to the model. Then, three-dimensional reference data regarding to the model with the reference body attached thereto is obtained. Then, grid patterned light is emitted onto the model with the reference body attached thereto to obtain reflection image regarding to the model with the reference body thereto. Then, three-dimensional shape is measured by applying bucket algorithm to the reflection image regarding to the model with the reference body attached thereto, and measurement image is obtained from the three-dimensional shape. Then, the measurement image and previously obtained three-dimensional reference data are matched with reference to a surface of the model. Then, reference position of the target in the three-dimensional reference data is compared with estimated position of the target, which is estimated by the reference body in the measurement image. Then, a position difference between the reference position of the target and the estimated position of the target is calculated. Then, a compensation relation equation for compensating the position difference is obtained. Then, the matching of the surgical operation image is corrected by using the compensation relation equation.

Advantageous Effects

According to the present invention, the three-dimensional image such as CT are obtained regarding to the operation spot of a patient before operation, three-dimensional shape of the operation spot is measured by applying bucket algorithm to pattern images according to the grid patterned light, and the three-dimensional shape and the three-dimensional image are matched. In this case, the previous matching may be performed by using the measurement image measured before incising the operation spot, and the precise matching may be performed by using the measurement image after incising the operation spot. Alternatively, the previous matching may be performed by using the measurement image after incising the operation spot and by receiving manual input from an operator, and the precise matching may be performed by using ICP algorithm.

Regarding to this, the model for being inspected is manufactured, the reference body is formed at the model, the reference data and the measurement image are obtained and matched, and the change of the position of the target is analyzed to verify and compensate the matching.

Further, when at least three reference bodies, each of which has a pole shape, are employed, the position of the target estimated from the measurement image becomes more exact, so that the verification and the compensation may be performed more exactly.

EMBODIMENTS OF THE INVENTION

This invention may be embodied in many different forms, and will be described with reference to the accompanying drawings. But this invention should not be construed as limited to the embodiments set forth herein, but should be understood to include every modifications, equivalents and substitutes The terms such as 'first', 'second', etc. may be used for various elements but the elements should not limited by the terms. The terms may be used only for discriminating one element from others. For example, a first element may be named as a second element, and the second element may be named as the first element within the present invention.

The terms used in the present application are only to explain the specific embodiment and is not intended to limit the present invention. The terms "a", "an" and "the" mean "one or more" unless expressly specified otherwise. The terms "including", "comprising", etc., are to designate features, numbers, processes, structural elements, parts, and combined component of the application, and should be understood that it does not exclude one or more different features, numbers, processes, structural elements, parts, combined component.

The technical term or the scientific term that will be used in the specification has the same meaning as a person skilled in the art commonly understood unless defined differently.

The terms defined in a commonly used dictionary should be understood as the context, and should not be understood ideally or excessively unless defined differently.

Hereinafter, preferred embodiments of the present invention will be explained referring to figures.

Figure 1:
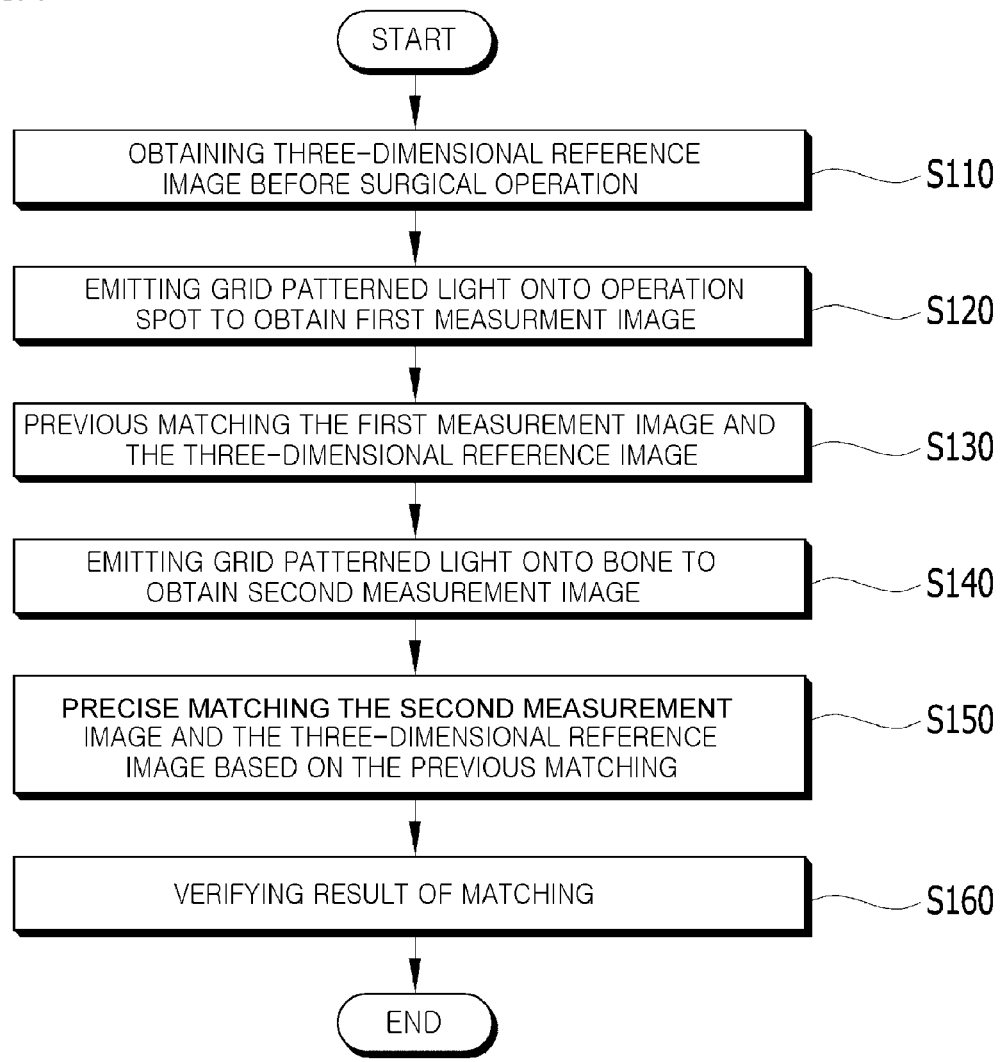
FIG. 1 is a flow chart showing a method of matching a surgical operation image according to an exemplary embodiment of the present invention.

FIG. 1 is a flow chart showing a method of matching a surgical operation image according to an exemplary embodiment of the present invention.

Referring to FIG. 1, a three-dimensional reference image is captured before a surgical operation for surgical operation image matching according to an embodiment of the present invention (S110).

In detail, the three-dimensional reference image regarding to operation spot for example an ear region is captured before operation. The three-dimensional reference image may include a computer tomography (CT) image generally captured in a hospital for diagnosis and treatment. Further, the three-dimensional reference image may include other three-dimensional images such as a magnetic resonance imaging (MRI).

Then, a grid patterned light is emitted toward an operation spot to capture a first measurement image (S120).

In detail, the grid patterned light is emitted to the operation spot to get a first reflection image of the operation spot, and the three-dimensional shape is measured by applying a bucket algorithm to the first reflection image to obtain the first measurement image from the three-dimensional shape.

Figure 2:
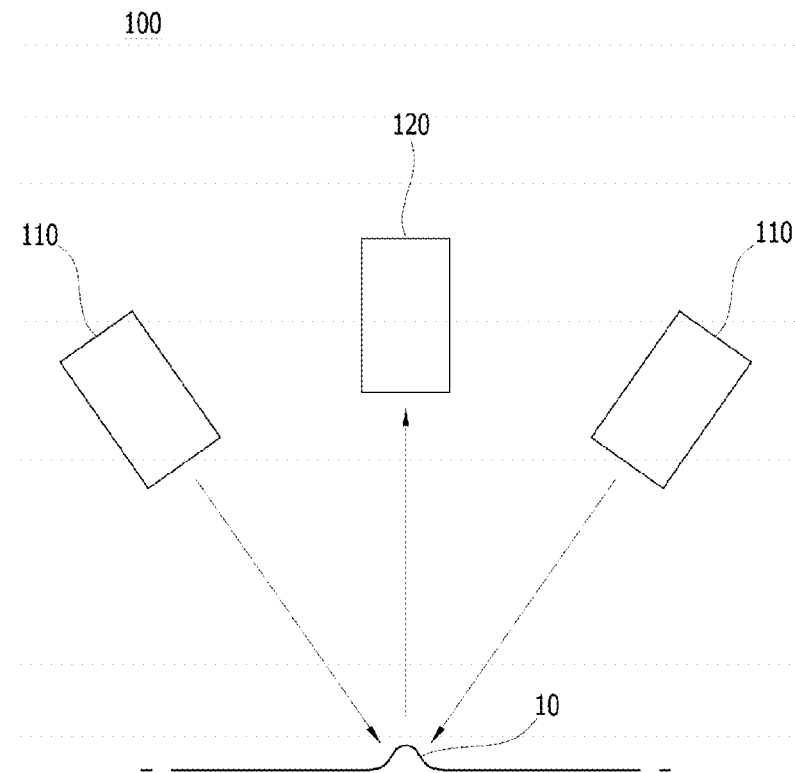
FIG. 2 is a conceptual view showing an apparatus of measuring a three-dimensional shape for explaining a process of obtaining a measuring image by capturing an image of region of operation.

FIG. 2 is a conceptual view showing an apparatus of measuring a three-dimensional shape for explaining a process of obtaining a measuring image by capturing an image of region of operation.

Referring to FIG. 2, an apparatus of measuring a three-dimensional shape 100 for obtaining the first measurement image by emitting the grid patterned light onto the operation spot may include a projecting part 110, an image capturing part 120 and a central control part (not shown).

The projecting part 110 may be tilted with respect to the operation spot 10, and emits the grid patterned light onto the operation spot 10. For example, the projecting part 110 may include a lighting unit, a grid unit, a grid shifting unit and a condensing lens for emitting grid patterned light. The lighting unit generates light. The grid unit transforms the light generated by the lighting unit into the grid patterned light with grid pattern. The grid shifting unit is connected to the grid unit to shift grid unit. A piezoelectric transferring unit or a minute linear transferring unit may be employed as the grid shifting unit. The condensing lens is disposed under the grid unit so that the grid patterned light passing through the grid unit is condensed to the operation spot 10.

For example, the projecting part 110 emits the grid patterned light onto the operation spot 10 N-times with the grid unit shifted N-times by the grid shifting unit, and the image capturing part 120 captures N-number of patterned images reflected from the operation spot 10, wherein 'N' is a natural number, for example three or four.

The projecting part 110 may employ an analog pattern projector using PZT transferring unit. Alternatively, the projecting part 110 may employ a digital pattern projector using digital micro-mirror device (DMD).

The number of the projecting part 110 may be plural. In this case, the grid patterned light emitted onto the operation spot 10 is emitted in various directions so that various patterned images may be captured. Therefore, an error induced by a shadow region corresponding to a shadow of the operating spot 10 or a saturated region with saturated brightness may be prevented. For example, when three projecting parts 110 are arranged at vertexes of an equilateral triangle with the image capturing part 120 at a center thereof, the three grid patterned lights may be emitted onto the operation spot 10 in different directions, and when four projecting parts 110 are arranged at vertexes of a square with the image capturing part 120 at a center thereof, the four grid patterned lights may be emitted onto the operation spot 10 in different directions.

Alternatively, the number of the projecting part 110 may be only one. In this case, the grid patterned light is emitted onto the operating spot 10 in only one direction, so that an error may be generated due to the shadow region or the saturated region. However, the error may be so small not to influence the image matching that will be described.

The image capturing part 120 is disposed over the operation spot 10 to receive light reflected from the operating spot 10 to capture the image of the operation spot 10. That is, the image capturing part 120 captures light generated by the projecting part 110 and reflected by the operation spot 10 to capture a planar image of the operation spot 10.

For example, the image capturing part 120 may include a camera, an image formation lens and a filter. The camera receives light reflected by the operation spot 10 to capture the planar image of the operation spot 10, and a CCD camera or a CMOS camera may be employed as the camera. The image forming lens is disposed under the camera to form image using the light reflected by the operation spot 10 at the camera. The filter is disposed under the image forming lens to filter the light reflected from the operation spot 10 to provide the image forming lens with the filtered light. The filter may include at least one of a frequency filter, a color filter and an intensity adjusting filter.

The control part is connected to the projecting part 110 and the image capturing part 120 to control the projecting part 110 and the image capturing part 120. The control part measures and calculates the three-dimensional image of the operation spot 10 by using the pattern image captured by the image capturing part 120.

Not shown in figure, the apparatus of measuring a three-dimensional shape 100 may further include a zig part for fixing the above constitution.

Further, when employing an analog pattern projector, the apparatus of measuring a three-dimensional shape 100 may adjust a spot of laser to be disposed at a center of the camera by using the offset-axis laser. When employing a digital pattern projector, the projecting part 110 project directly so that the spot may be adjusted to be disposed at the center of the camera.

Referring again to FIG. 1, the first measurement image and the three-dimensional reference image are previously matched (preliminary registration) (S130).

In detail, the first measurement image obtained in the step (S120) through emitting grid patterned light onto the operation spot 10 and the three-dimensional reference image obtained before an operation in the step (S110) are firstly matched. This first matching is a previous matching performed before a precise matching that will be explained, and corresponds to a coarse matching.

Figure 3:
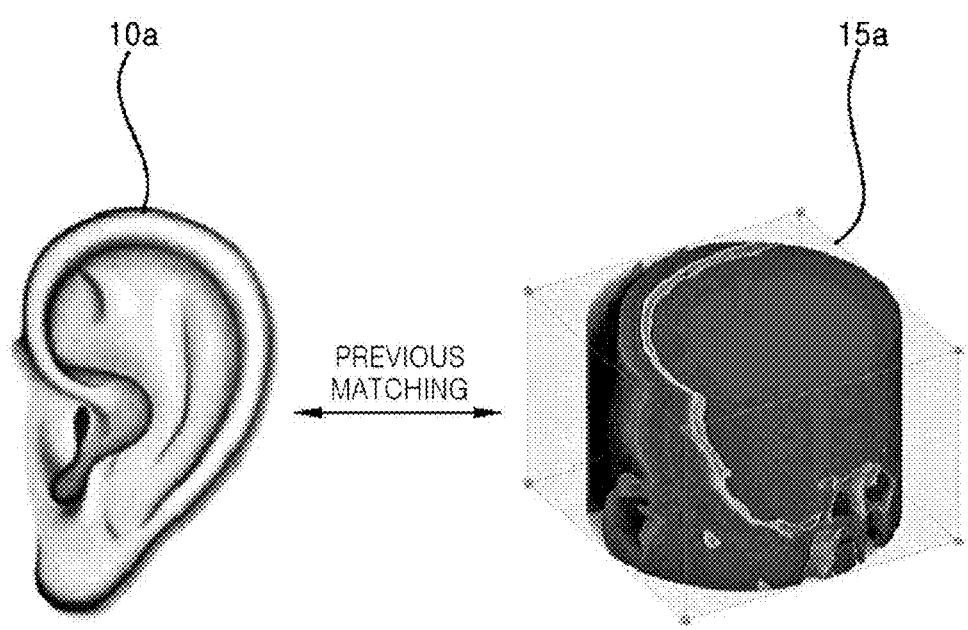
FIG. 3 is a conceptual view showing a process of previous matching in FIG. 1.

FIG. 3 is a conceptual view showing a process of previous matching in FIG. 1.

Referring to FIG. 3, for example, when the operation spot 10 is an ear region, the first measurement image 10*a* obtained by emitting the grid patterned light onto the ear region and the three-dimensional reference image 15*a* that is an CT image obtained before operation are previously matched.

Referring again to FIG. 1, a grid patterned light is emitted onto a bone to get a second measurement image S140.

In detail, when the operation spot 10 is incised for the operation, the grid patterned light is emitted onto the bone corresponding to the operation spot 10, the second reflection image regarding to the bone corresponding to the operation spot in accordance with the grid patterned light, three-dimensional shape is measured by applying bucket algorithm to the second reflection image regarding to the bone corresponding to the operation spot, and the second measurement image is obtained from the three-dimensional shape.

The process of obtaining the second measurement image is substantially the same as the process of obtaining the first measurement image except for the fact that the measurement target is the bone corresponding to the operation spot 10 after the operation spot 10 is incised, so that any repetitive explanation will be omitted.

Referring again to FIG. 1, the second measurement image and the three-dimensional reference image are precisely matched (fine registration) based on the result of the previous matching (S150).

In detail, the second measurement image obtained by emitting the grid patterned light onto the bone corresponding to the operation spot 10 in the step S140 and the three-dimensional reference image obtained in the step S110 before the operation are secondly matched. The secondary matching corresponds to a fine matching.

Figure 4:
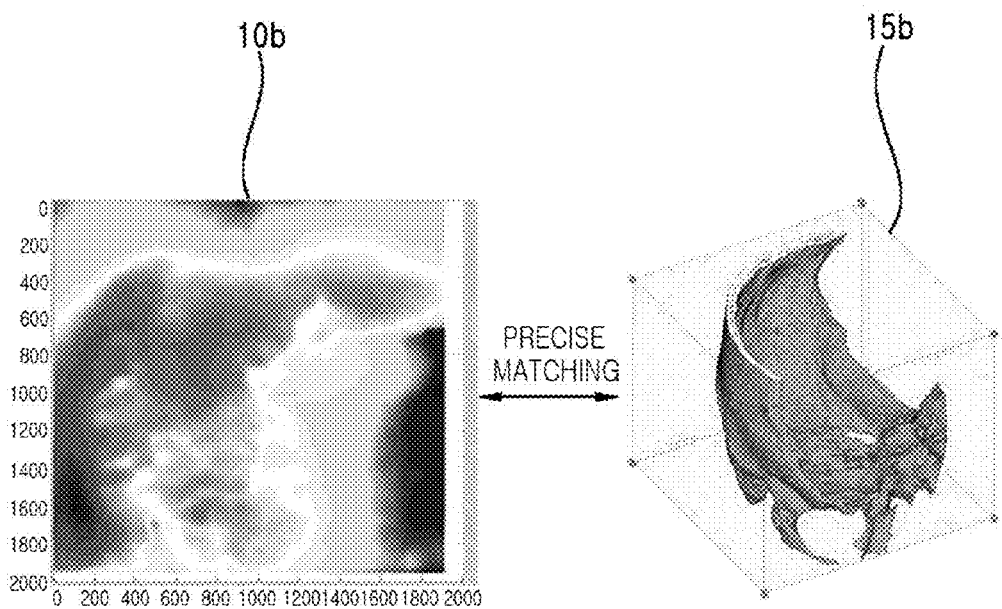
FIG. 4 is a conceptual view showing a process of precise matching in FIG. 1.

FIG. 4 is a conceptual view showing a process of precise matching in FIG. 1.

Referring to FIG. 4, for example, when the operation spot 10 is an ear region, the second measurement image 10*b* regarding to the bone corresponding to the ear region, which is obtained by emitting the grid patterned light after the ear region is incised, and the three-dimensional reference image 15*b* regarding to the bone corresponding to the ear region, which is CT image obtained before the operation are precisely matched.

Referring again to FIG. 1, the result of precisely matching may be optionally verified (S160).

In detail, a verifying tool makes contact with the bone corresponding to the operation spot 10, and the verifying tool is checked through a screen generated by the precise matching if the verifying tool is in touch with the bone. In this case, when the verifying tool is in touch with the bone in the screen, the matching is determined to be effective.

Figure 5:
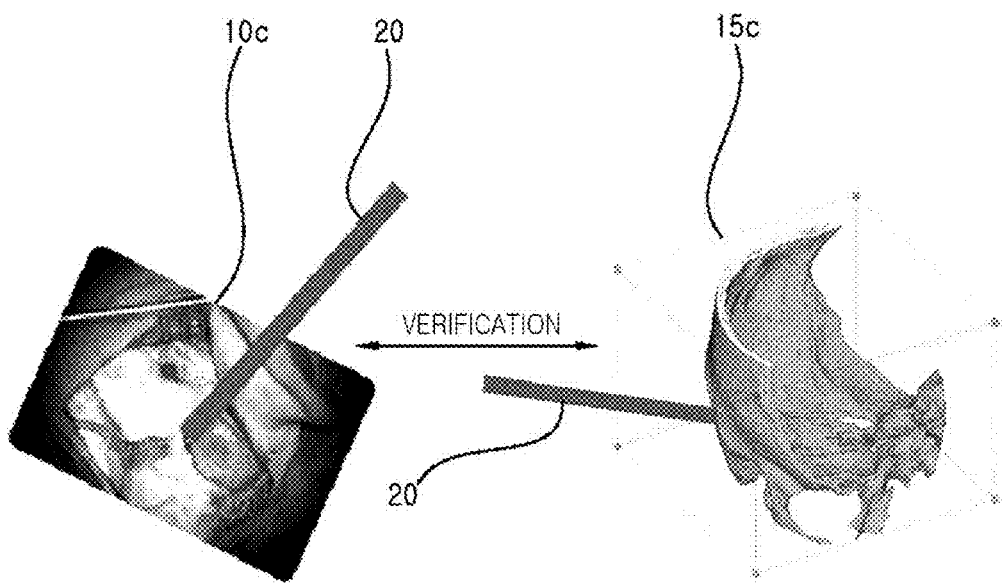
FIG. 5 is a conceptual view showing a process of verifying precise matching in FIG. 1.

FIG. 5 is a conceptual view showing a process of verifying precise matching in FIG. 1.

Referring to FIG. 5, when the operation spot 10 is an ear region, the verifying tool 20 is verified if the verifying tool 20 is in contact with the bone (15*c*) corresponding to the ear region in the three-dimensional reference image 15*b* regarding to the bone corresponding to the bone, which is a CT image obtained before the operation.

Figure 6:
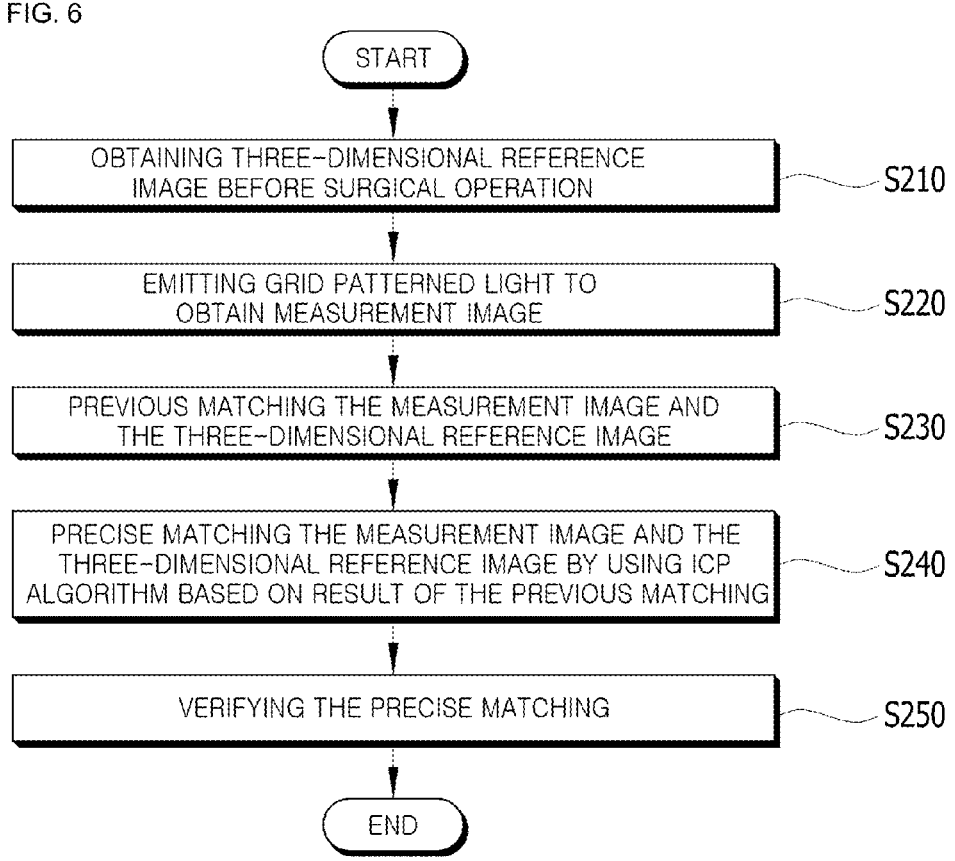
FIG. 6 is a flow chart showing a method of surgical operation image matching according to another embodiment of the present invention.

FIG. 6 is a flow chart showing a method of surgical operation image matching according to another embodiment of the present invention.

Referring to FIG. 6, a three-dimensional reference image is obtained before operation in order for a surgical operation image matching according to another embodiment (S210).

This step is substantially the same as the step S110 explained referring to FIG. 1, in which three-dimensional image is obtained, so that any repetitive explanation will be omitted.

Then, a grid patterned light is emitted onto a bone to obtain a measurement image (S220).

This step is substantially the same as the step S120 explained referring to FIG. 1, in which measurement image is obtained, so that any repetitive explanation will be omitted.

Then, the measurement image and the three-dimensional reference image are matched (S230).

In detail, the measurement image obtained in the step S220 by emitting grid patterned light onto the bone corresponding to the operation spot 10 and the three-dimensional reference image obtained in the step of S210 are firstly matched, and the matching is input from an operator. This first matching is a coarse matching.

Figure 7:
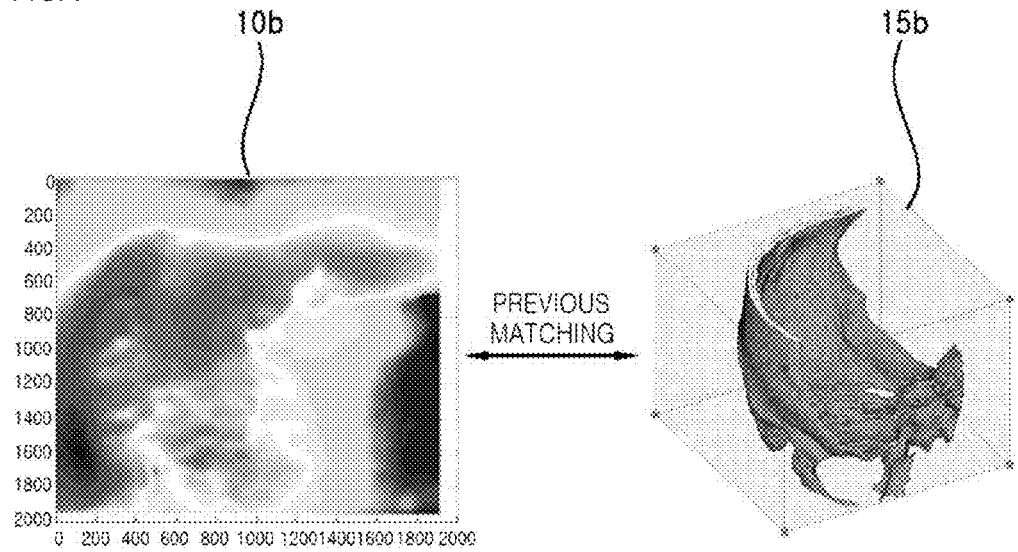
FIG. 7 is a conceptual view showing a previous matching in FIG. 6.

FIG. 7 is a conceptual view showing a previous matching in FIG. 6.

Referring to FIG. 7, for example, when the operation spot 10 is an ear region, the measurement image 10b regarding to the ear region, which is obtained by emitting the grid patterned light onto the ear region after the ear region is incised, and the three-dimensional reference image 15b that is an CT image obtained before operation are previously matched, and the matching is input from an operator.

Referring again to FIG. 6, the measurement image and the three-dimensional reference image are precisely matched by using iterative closet points (ICP) algorithm based on the previous matching (S240).

The ICP algorithm is the algorithm for matching three-dimensional scene, and widely used in various application fields, which is well known, so that detailed explanation will be omitted.

Then, the result of precisely matching may be optionally verified (S250).

This step is substantially the same as the step of S160 in which the precisely matching is verified so that any repetitive explanation will be omitted.

The matching of a surgical operation image according to the present invention will be verified and compensated as follows.

Figure 8:
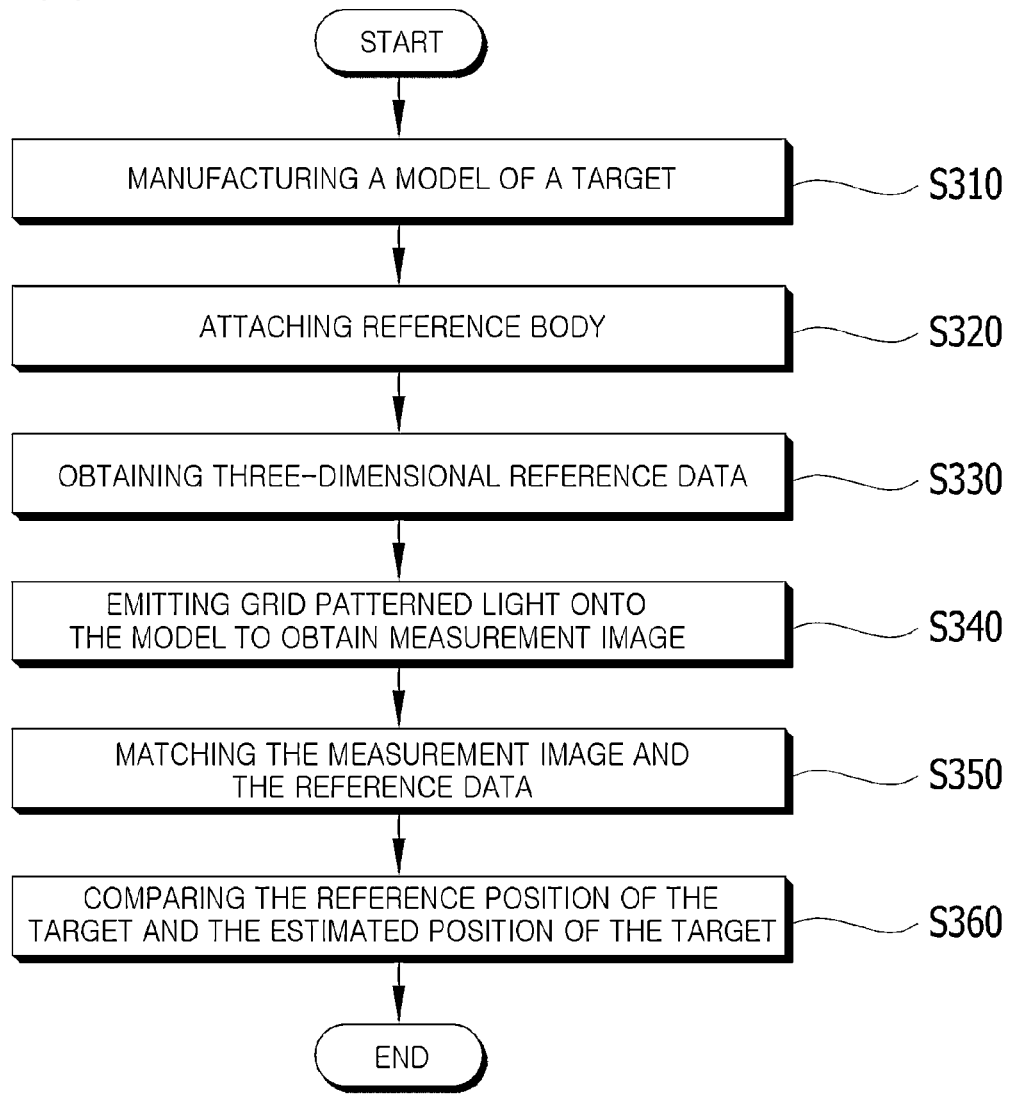
FIG. 8 is a flow chart showing a method of verifying a surgical operation image matching according to an embodiment of the present invention.
Figure 9:
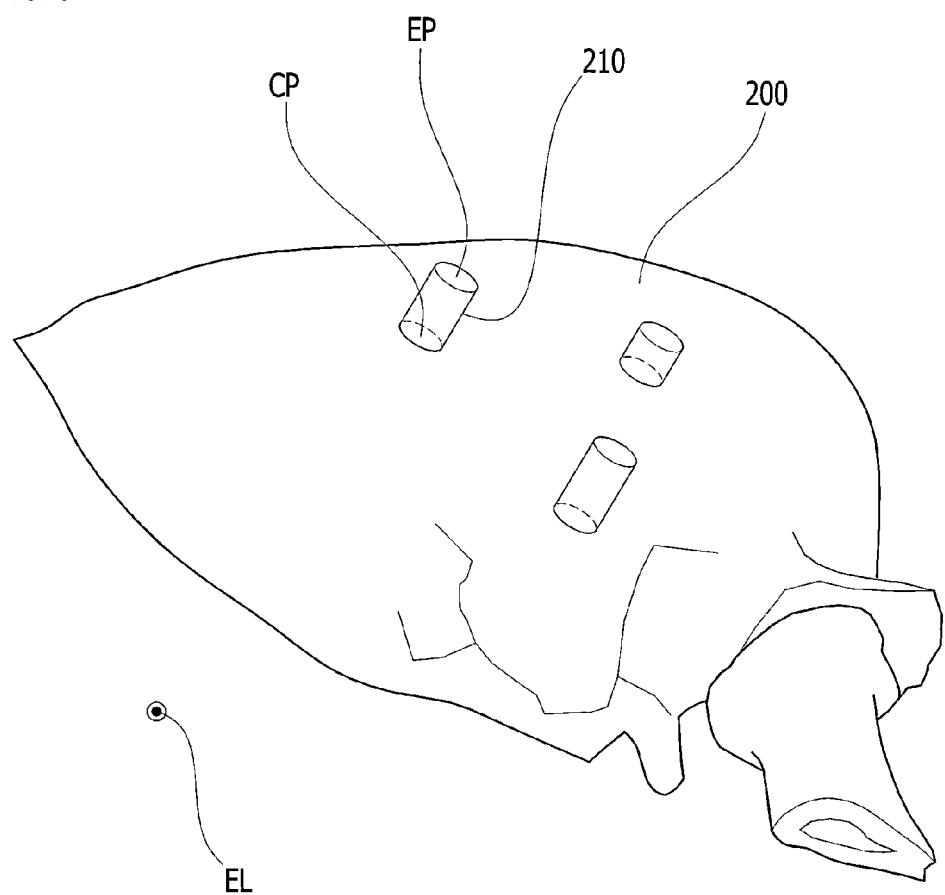
FIG. 9 is a perspective view showing an example of a model used in the verifying method in FIG. 8.

FIG. 8 is a flow chart showing a method of verifying a surgical operation image matching according to an embodiment of the present invention, and FIG. 9 is a perspective view showing an example of a model used in the verifying method in FIG. 8.

Referring to FIG. 8 and FIG. 9, a model (200) of a verification target is manufactured in order to verify if the matching of the surgical operation image is correct (S310).

The model 200 includes an operation spot of a patient. For example, the model 200 may be formed copying an ear region. The model 200 may be formed copying the bone exposed after incising the ear region as explained referring to FIG. 1 through FIG. 4.

Then, a reference body 210 is formed at the model 200 (S320).

The reference body 210 is referenced for calculating a relative position of target that will be explained. For example, the reference body 210 may have a pole shape as shown in FIG. 9. The number of reference body 210 may be at least three in order to exactly estimate the position of the target.

Then, three-dimensional reference data is obtained regarding to the model 200 with the reference body 210 (S330). The three-dimensional reference data may include for example three-dimensional reference image.

For an embodiment, the three-dimensional reference data may be obtained from the model 200 and CAD information recording the shape of the reference body 210. The CAD information includes a design reference information of the model 200 and the reference body 210. Alternatively, the three-dimensional reference data may be obtained from a precise shape information of the model 200 and the reference body 210, which is measured by a precise measuring apparatus.

Then, a grid patterned light is emitted onto the model 200 with the reference body 210 to obtain the measurement image (S340).

In detail, the grid patterned light is emitted onto the model 200 with the reference body 210 to capture reflection image regarding to the model 200 with the reference body 210, three-dimensional shape is measured by applying bucket algorithm to the reflection image regarding to the model 200 with the reference body 210, and the measurement image is obtained from three-dimensional shape. This process corresponds to measuring process using the apparatus of measuring a three-dimensional shape 100 explained referring to FIG. 1 and FIG. 2, and any repetitive explanation will be omitted.

Then, the measurement image and the three-dimensional reference data are matched (or registered) with reference to a surface of the model 200 (S350).

The matching may correspond to the step (S150) of precise matching explained referring to FIG. 1 and FIG. 4.

Then, the reference position of a target in the three-dimensional reference data and the estimated position (EL) of the target, which is estimated by the reference body 210 in the measurement image are compared with each other (S360).

The target may be the operation spot. The reference position of the target may be obtained by applying the position of the operation spot obtained through CT image, etc. to the three-dimensional reference data such as the CAD information, and may be a position where the target is theoretically disposed. The estimated position (EL) of the target may be the position estimated relatively from the reference body 210 in the measurement image. When FIG. 9 corresponds to the measurement image, the estimated position (EL) of the target may be obtained with reference to a contact point (CP) where the end point (EP) of the reference body 210 or the reference body 210 meets the surface of the model 200 when the reference body 210 has the pole shape as shown in FIG. 9.

The difference between the reference position and the estimated position becomes smaller, the error of the above described matching method becomes smaller.

For an embodiment, after comparing the reference position of the target in the three-dimensional reference data and the estimated position of the target, which is estimated by the reference body, the difference between the reference position of the target and the estimated position of the target may be calculated and checked if the difference of the position is within a reference value. When the difference of the position is within the reference value, the matching method is determined to be good, and when the difference of the position is out of the reference value, the matching method is determined to be bad.

On the other hand, by using the difference of the position in accordance with the verifying method, the error of the matching method may be corrected.

That is, the difference between the reference position of the target and the estimated position of the target is calculated, a compensation relation equation for compensating the position difference is obtained, and the matching of the real surgical operation image is compensated by using the compensation relation equation. In order to obtain the compensation relation equation, the position of the reference body 210 is changed and previous processes are repetitively performed to get various raw data.

According to the present invention, the three-dimensional image such as CT are obtained regarding to the operation spot of a patient before operation, three-dimensional shape of the operation spot is measured by applying bucket algorithm to pattern images according to the grid patterned light, and the three-dimensional shape and the three-dimensional image are matched. In this case, the previous matching may be performed by using the measurement image measured before incising the operation spot, and the precise matching may be performed by using the measurement image after incising the operation spot. Alternatively, the previous matching may be performed by using the measurement image after incising the operation spot and by receiving manual input from an operator, and the precise matching may be performed by using ICP algorithm.

Regarding to this, the model for being inspected is manufactured, the reference body is formed at the model, the reference data and the measurement image are obtained and matched, and the change of the position of the target is analyzed to verify and compensate the matching.

Further, when at least three reference bodies, each of which has a pole shape, are employed, the position of the target estimated from the measurement image becomes more exact, so that the verification and the compensation may be performed more exactly.

The detailed description of the present invention is described with regard to the preferable embodiment of the present invention, however, a person skilled in the art may amend or modify the present invention within the spirit or scope in the following claim of the present invention.

What is claimed is:

1. A method of verifying a surgical operation image matching in which a three-dimensional reference image of a target acquired before surgery and a three-dimensional measurement image of the target are matched, the method comprising:
    obtaining by a shape measurement apparatus, three-dimensional reference image of a model including the surgical area, wherein the model is physically manufactured and a reference object is physically attached to the model;
    providing, by the shape measurement apparatus, grid patterned light onto the model and the reference object to obtain a reflection image of the model and the reference object;
    measuring, by the shape measurement apparatus, a three-dimensional shape of the model and the reference object by using the reflection image to obtain a three-dimensional measurement image of the model and the reference object from the three-dimensional shape;
    matching, by a processor, the three-dimensional measurement image of the model and the reference object and the three-dimensional reference image of the model and the reference object based on a surface of the model;
    obtaining, by the processor, a reference position of the target in the three-dimensional reference image of the model and the reference object and an estimated position of the target, wherein the estimated position of the target is a position estimated relatively from the reference object in the three-dimensional measurement image of the model and the reference object;
    comparing, by the processor, the reference position of the target with the estimated position of the target; and
    verifying, by the processor, the surgical operation image matching based on a result of the comparison.

2. The method of claim 1, wherein the reference object has a pole-shape.

3. The method of claim 1, wherein a number of the reference object is at least three.

4. The method of claim 1, wherein the three-dimensional reference image is obtained from the model and at least one of CAD information and precise measurement information of both the model and the reference object.

5. The method of claim 1, wherein the step of verifying, by the processor, the surgical operation image matching further includes:
    calculating, by the processor, a position difference between the reference position of the target and the estimated position of the target;
    checking, by the processor, if the position difference is within a reference value; and
    when the position difference is within the reference value, the surgical operation image matching is determined to be good and when the position difference is out of the reference value, the surgical operation image matching is determined to be bad.

6. A method of compensating a surgical operation image matching in which a three-dimensional reference image of a target acquired before surgery and a three-dimensional measurement image of the target are matched, the method comprising:
    obtaining, by a shape measurement apparatus, three-dimensional reference image of a model including the surgical area, wherein the model is physically manufactured and a reference object is physically attached to the model;
    providing, by the shape measurement apparatus, grid patterned light onto the model and the reference object to obtain a reflection image of the model and the reference object;
    measuring, by the shape measurement apparatus, a three-dimensional shape of the model and the reference object by using the reflection image to obtain a three-dimensional measurement image of the model and the reference object from the three-dimensional shape;
    matching, by a processor, the three-dimensional measurement image of the model and the reference object and the three-dimensional reference image of the model and the reference object based on a surface of the model;
    obtaining, by the processor, a reference position of the target in the three-dimensional reference image of the model and the reference object and an estimated position of the target, wherein the estimated position of the target is a position estimated relatively from the reference object in the three-dimensional measurement image of the model and the reference object;
    comparing, by the processor, the reference position of the target with the estimated position of the target;
    calculating, by the processor, a position difference between the reference position of the target and the estimated position of the target;
    obtaining, by the processor, a compensation relation equation for compensating the position difference; and
    correcting, by the processor, the surgical operation image matching by using the compensation relation equation.

7. The method of claim 6, wherein the compensation relation equation is obtained by changing a position of the reference object.

* * * * *